United States Patent
Bañuls Polo et al.

(10) Patent No.: US 8,236,367 B2
(45) Date of Patent: Aug. 7, 2012

(54) METHOD OF CHEMICALLY MODIFYING POLYMER SURFACES INTENDED FOR IMMOBILIZING MOLECULES

(75) Inventors: María del Carmen Bañuls Polo, Valencia (ES); Francisco García Piñón, Valencia (ES); Ángel Maquieira Catalá, Valencia (ES); Rosa Puchades Pla, Valencia (ES)

(73) Assignee: Universidad Politecnica de Valencia, Valencia (ES)

( * ) Notice: Subject to any disclaimer, the term of this patent is extended or adjusted under 35 U.S.C. 154(b) by 820 days.

(21) Appl. No.: 12/317,713

(22) Filed: Dec. 26, 2008

(65) Prior Publication Data

US 2009/0181442 A1 Jul. 16, 2009

Related U.S. Application Data

(63) Continuation of application No. PCT/ES2007/000351, filed on Jun. 14, 2007.

(30) Foreign Application Priority Data

Jun. 28, 2006 (ES) .................................. 200601802

(51) Int. Cl.
*B05D 3/00* (2006.01)
(52) U.S. Cl. ................... 427/2.13; 437/2.11; 435/287.1; 435/287.9; 525/350; 525/467; 528/486; 528/487; 528/491
(58) Field of Classification Search ............. 427/2.11, 427/2.13; 435/287.1, 287.9; 525/350, 467; 528/486, 487, 491
See application file for complete search history.

(56) References Cited

U.S. PATENT DOCUMENTS

2005/0101006 A1   5/2005   Cheng et al.
2009/0128822 A1*  5/2009   Yamamichi et al. .......... 356/445

FOREIGN PATENT DOCUMENTS

WO   WO 2007/015556   *   2/2007

OTHER PUBLICATIONS

Zammatteo, et al., Comparison between Different Strategies of Covalent Attachment to DNA . . . Analytical Biochemistry, 280, 143-150 (2000).
Cheung, et al., Making and Reading Microarrays; Nature Genetics Supplement, vol. 21, pp. 15-19, (1999).
Kido, et al., Disc-based Immunoassay Microarrays, Analytica Chimica Acta, 411 (2000) 1-11.
Chan, et al., Polymer surface modification by plasmas and photon, Surface Science reports 24 (1996) 1-54.
Soper, et al., Surface modification of polymer-based microfluidic devices, Analytica Chimica Acta, 470 (2002) 87-90.
Cheng, et al., Direct-write laser micromachining and universal surface modification . . . Sensors and Actuators B 99 (2004) 186-196.
Xu, et al., Solid-Phase Reversible Immobilization in Microfluidic Chips . . . Analytical Chemistry, vol. 75, No. 13 (2003).

* cited by examiner

*Primary Examiner* — David W Wu
*Assistant Examiner* — Robert Jones, Jr.
(74) *Attorney, Agent, or Firm* — Klauber & Jackson, LLC

(57) ABSTRACT

The method comprises chemical modification of an optionally metallized polymer surface, for example a polycarbonate surface or a polymethacryllate surface functionalized with amino groups, said surfaces being optionally metallized, by treating said polymer surface with a mercaptoalkanoic acid or the salts or derivates thereof. The surfaces obtained by said method may be used as solid supports for immobilizing biomolecules, such as nucleic acids, proteins or membranes.

21 Claims, No Drawings

US 8,236,367 B2

METHOD OF CHEMICALLY MODIFYING POLYMER SURFACES INTENDED FOR IMMOBILIZING MOLECULES

RELATED APPLICATIONS

The present application is a Continuation of co-pending PCT Application No. PCT/ES2007/000351 filed Jun. 14, 2007, which in turn, claims priority from Spanish Application Serial No. P200601802 filed Jun. 28, 2006. Applicants claim the benefits of 35 U.S.C. §120 as to the PCT application and priority under 35 U.S.C. §119 as to said Spanish application, and the entire disclosures of both applications are incorporated herein by reference in their entireties.

FIELD OF THE INVENTION

The present invention relates to a method for chemically modifying optionally metalized polymer surfaces comprised of polycarbonate or polymethacrylate, it being possible for said surfaces to be used as solid supports for immobilizing biomolecules, such a nucleic acids or proteins.

BACKGROUND OF THE INVENTION

Microarrays technology, based on receptor-analyte interaction, is replacing the conventional assays using gels, filters and columns, with glass chips capable of storing tens of thousands of probes (nucleic acid sequences), proteins, etc, which provide information on the levels of gene expression, protein synthesis, single nucleotide polymorphisms or SNPs, etc.

The surfaces employed for microarrays must advantageously be flat and even, so as to make it possible to anchor of a large number (e.g. hundreds or thousands) of spatially arranged molecules (probes, proteins, etc.). The detection and quantification of results is carried out by means of fluorescence or colorimetry and, to a lesser extent, by mass spectroscopy, using molecules functionalized with a suitable marker for this purpose. The markers most often used are fluorophores with excitation wavelengths of around 450 nm and emissions within the 500 nm-800 nm range.

Due to its optical transparency, low autofluoresence, chemical properties, thermal stability and price, glass if the reference material employed as a support in this technology, By means of chemical modification, via silanization, specific functional groups can be added, such as amine-epoxy-carboxylic acid- or aldehyde groups (Cheung, V G, et al. *Nature Genetics* (suppl), 1999, 21, 15-19; Zammatteo, N. et al, *J. Analyt. Biochem,* 2000, 283, 143-150), which make the covalent anchoring of oligonucleotides or single-stranded DNA (ssDNA) molecules possible for the subsequent analysis thereof.

However, the great interest in the study of new supports and the large market existing in this field of work has led to the search for new alternative materials. Of all these materials, synthetic polymer materials display highly attractive chemical and mechanical properties, a good price, a high degree of flexibility and biocompatibility and good optical and mechanical properties, as well as being easy to manufacture. In addition thereto, they can be used as interactive supports, given that they increase the working capacity on affording the possibility of incorporating the treatment of the sample and the detection of the results. Similarly, detection techniques other than fluorescence can be used, thus making the assays faster and simpler. For all of the abovementioned reasons, polymer materials have become an alternative to glass for the manufacture of microarrays.

Apart from the above, the development of microelectromechanical systems for bioassays (BioMEMS) focuses many of the applications thereof on Genomics and Proteomics. This type of devices integrates chemical assays with the preparation of the sample and the detection thereof (results readout). For the manufacture thereof, synthetic polymer materials (e.g. polycarbonates, polymethacrylates, polystyrenes, polyamides, polysiloxanes, etc) or natural materials (silicon, silicon oxide, etc.), these latter materials coming from the electronics industry, are generally used.

Audio-video compact discs (CDs) are a promising platform for building this type of devices (EP 1189062; Kido, H. et al., *Analytica Chimica Acta,* 2000, 411, 1-11). A standard CD is comprised of a polycarbonate base on which the information is recorded, coated with a metal layer of aluminum, nickel, gold or silver, or rather with a layer of light-sensitive dye, protected by a polymethacrylate coating. One of the most outstanding advantages of CDs as supports for microarrays is the large surface area available, low background fluorescence, the use of materials of high optical and mechanical quality in their manufacture, their low price and their easy handling. Similarly, these supports afford the possibility of quadrangular, circular or spiral spatial organization of the probes and proteins printed, providing numerical information for identifying each spot, it being possible to use one of the sides of the CD for conducting the biochemical assays and the detection thereof, and the other side for saving the information, the results being read in all cases by means of modified CD-readers (U.S. Pat. No. 6,395,562 and WO2003/087827). The aforesaid could be applied to DVDs, given that they are of the same composition as CDs.

Chemically modifying polymer surfaces for the purpose of fine-tuning supports for chemical assays has still as yet not been developed to any great degree. This field of work has been approached by using different strategies, the techniques most employed being based on the plasma, flame, electrical discharge, surface grafting, chemical reaction and vapor deposition treatment (Chan. C M., *Polymer Surface Modification and Characterization,* 1993, Munich:Hansen).

Studies have been published describing surface modifications of different types of polymers (US2002/0197467). A study has been made of the surface modification of methyl polymethacrylate by means of aminolysis of the methyl ester with lithium amide in aliphatic diamines and the application thereof in devices for microfluids (Soper, S. A. et al., *Analytica Chimica Acta,* 2002, 470, 87-99; *Anal. Chem.,* 2003, 75, 2975-84). There are also other examples of surface modification of methyl polymethacrylate based on the reduction of the ester groups followed by a treatment with different organosilanes (Cheng J-Y., et al, *Sensors & Actuators B*99, 2004, 186-96). One drawback of these methods lies in the need of working with organic solvents which modify the properties of the plastic.

Surface modification methods for polycarbonate have also been described. Most of these methods use the oxidation/sulphonation of the rings or rather the hydrolysis of the carbonate (e.g. WO99/35499, EP0487854). These methods are, however, not very effective.

Despite the different surface modifying methods described in the state of the art, a great need still as yet exists of designing alternative methods for the chemical modification of polymers which will make it possible to provide surfaces of the desired properties whist ensuring that the optical and mechanical properties of the original polymer will remain unchanged.

BRIEF DESCRIPTION OF THE INVENTION

This invention provides a alternative method for chemically modifying polymer surfaces comprised of optionally metalized polycarbonate (PC) or polymethacrylate (PMMA) surfaces by means of using some specific reagents which will make it possible to carry out some fast and simple derivatization protocols which will provide some homogeneous surfaces whilst also optimally retaining the optical and mechanical properties of the derivatized support or surface. These characteristics are key to the later use thereof in electromechanical devices for the covalent anchoring of biomolecules, for example, nucleic acid, protein, membrane probes, etc. in assays, including genomic or proteomic assays. More specifically, this invention makes the covalent immobilizing of the aforementioned biomolecules possible on said modified polymer surfaces with terminal thiol groups by means of disulphide bonds, or on said metalized polymer surfaces modified with terminal acid groups by means of amide or ester bonds.

Therefore, one aspect of this invention relates to a method of chemically modifying an optionally metalized polymer surface selected from among (i) a PC surface functionalized with primary amino groups or with molecules comprising terminal primary amino groups (ii) a PMMA surface functionalized with molecules comprising terminal primary amino groups (iii) a metalized PC surface, and (iv) a metalized PMMA surface, which consists of putting said optionally metalized polymer surface though a treatment with a mercaptoalkanoic acid, the salts or derivatives thereof.

In another regard, this invention relates to a method of chemically modifying a PMMA surface which comprises:
a) reacting said PMMA surface with a reducing agent in the presence of cyclohexane as a solvent so as to obtain alcohol groups; and
b) reacting the product resulting from stage a) with an organosilane which comprises a terminal thiol group in an alcohol solution.

In another regard, this invention relates to a solid support comprising an optionally metalized PC or PMMA surface chemically modified according to any of the aforesaid methods provided by this invention. This solid support can be used for immobilizing biomolecules.

Therefore, in another regard, this invention relates to a solid support comprising an optionally metalized PC or PMMA surface chemically modified according to any of the aforesaid methods provided by this invention, on which at least one biomolecule has been affixed. In one particular embodiment, on said solid support treated according to the surface modifying method provided by this invention, a number of biomolecules are affixed in an established order and arrangement comprising an array or microarray.

In another regard, this invention relates to a method for immobilizing (anchoring) biomolecules on a solid support which consists of bringing said solid support comprising an optionally metalized PC or PMMA surface modified chemically according to any of the aforesaid methods provided by this invention, into contact with at least one biomolecule.

DETAILED DESCRIPTION OF THE INVENTION

In order to facilitate the comprehension of this invention, the meanings of some terms and phrases as used herein are explained in following.

The term "polycarbonate (PC) surface" refers to a surface comprised in full or in part of PC; in one particular embodiment, said PC polymer surface is a surface comprised of dimensional, smooth or substantially flat and even PC which is modifiable by way of its aromatic rings.

The term "polymethacrylate (PMMA) surface" refers to a surface comprised in full or in part of PMMA; in one particular embodiment, said PMMA polymer surface is a surface comprised of dimensional, smooth or substantially flat and even PMMA which is modifiable by way of its ester groups.

The terms "PC surface coated with a metallic layer" and "PMMA surface coated with a metallic layer" respectively refer to a PC or PMMA surface on which a thin layer comprised of a metallic material reactable with compounds comprising terminal thiol groups has been deposited.

The term "PC surface functionalized with amino groups" refers to a PC surface onto which amino groups ($-NH_2$) have been introduced as substituents in the aromatic structure of the PC.

The term "PC surface functionalized with molecules comprising terminal primary amino groups" refers to a PC surface onto which a molecule comprising a terminal amino group ($-NH_2$) has been introduced into the aromatic structure of the PC.

The term "PMMA surface functionalized with molecules comprising terminal primary amino groups" refers to a PMMA surface in which a molecule comprising a terminal amino group ($-NH_2$) has been introduced by way of the ester group constituting the PMMA structure.

The term "biomolecule" includes, in general, all that molecular substance originally from living beings, which also may have been synthesized or modified, in full or in part, by man. This term includes nucleic acids, proteins, substances which can be used in molecular recognition, membranes or other cell fragments of natural or synthetic origins, etc. Illustrative, non-limiting examples of such biomolecules include nucleic acids, proteins, antibodies, molecular receptors, enzymes, carbohydrates, cell membranes (cytoplasmic, nuclear or other cell organelle membranes) and other cell fragments of a natural or synthetic nature.

The term "nucleic acid" refers to a natural or synthetic sequence of nucleotides, for example DNA, gDNA, cDNA, RNA, etc.; in one particular embodiment, said nucleic acid is a probe.

The term "protein" refers to a molecular chain of amino acids, linked by covalent or non-covalent bonds. This term includes all forms of post-translational modifications, for example, glycosylation, phosphorylation, acetylation, etc. This term also includes proteins which carry out specific functions, for example, antibodies, enzymes, molecular receptors, etc.

The abbreviations EDC, DCC, NHS and NHSS stand for the following compounds:
EDC: 1-ethyl-3-(3-dimethylaminopropyl) carbodiimide
DDC: dicyclo-hexylcarbodiimide;
NHS: N-hydroxysuccinimide;
NHSS: sulfa-N-hydroxysuccinimide In one aspect, this invention relates to a method, referred to hereinafter as the invention method, for chemically modifying an optionally metalized polymer surface selected from among (i) a PC surface functionalized with primary amino groups or with molecules comprising terminal primary amino groups (ii) a PMMA surface functionalized with molecules comprising terminal primary amino groups (iii) a PC surface coated with a metal layer, and (iv) a PMMA surface coated with a metal layer, which consists of reacting said optionally metalized polymer surface with a mercaptoalkanoic acid of the following formula (I)

$$HS-(CH_2)_n-COOH \qquad (I)$$

where "n" is a whole number from 3 to 11;
the salts or derivatives thereof.

The term "salts" as employed herein includes any salt of the mercaptoalkanoic acid of formula (I), for example but not limited to, metal salts. The use of said salts would permit an electrostatic interaction with the $NH_3+$ groups possibly present in a biomolecule.

The term "derivative" as employed herein includes any compound which converts into said mercaptoalkanoic acid of formula (I) by means of hydrolysis, for example, an ester, an acid halide, an acid anhydride, an amide or a nitrile. The use of acid anhydrides and halides would facilitate the forming of the amide, whilst the use of esters would generally require their previously being hydrolyzed, for example with amides.

It will be obvious to any expert in the art that practically any salt or derivative of the mercaptoalkanoic acid of formula (I) which is not detrimental to the reaction entailed can be used for putting this invention into practice.

In one particular embodiment, the invention method comprises the use of a PC surface functionalized with amino groups. The functionalizing of PC surfaces with primary amino groups can be carried out by means of any method known to an expert in the art which allows amino groups to be introduced into the aromatic structure of the PC. In one particular embodiment, this functionalization can be carried out by means of a method consisting of the following stages:
  (i) nitration of the aromatic rings comprising the structure of the PC, and
  (ii) reduction of the nitro groups introduced in stage (i) in order to obtain the aforesaid amino groups.

Stage (i) [nitration] can generally be carried out by reacting said PC surface with nitric acid, whilst in stage (ii) [reduction], the nitro groups introduced in stage (i) are reduced by means of the use of a suitable reducing agent in a suitable solvent. Practically any reducing agent capable of reducing the nitro group to an amino group can be used; nevertheless, in one particular embodiment, said reducing agent is a metal hydride, a boron derivative, etc., such as $NaBH_4$, $LiAlH_4$, $BH_3$-THF, DIBAH, Red-Al, etc. As a solvent, any suitable inert solvent, such as, for example, an alcohol, can be used. In one particular embodiment, the reduction of the nitro groups is carried out using $NaBH_4$ in ethanol.

In another particular embodiment, the invention method comprises the use of a PC surface functionalized with molecules comprising terminal primary amino groups. The functionalizing of PC surfaces with molecules comprising a terminal amino group can be carried out by means of any method known to an expert in the art which will make it possible to introduce a molecule with a terminal amine group into the aromatic structure of the PC. In one particular embodiment, said functionalization is carried out by means of a method consisting of the following stages:
  a) chloromethylation of the aromatic rings comprising the structure of the PC, and
  b) nucleophilic replacement of the chloride groups present following stage a) by reacting with an aliphatic diamine The chloromethylation [stage a)] can be carried out by reacting said PC surface with a chloromethylating agent. Practically any chloromethylating agent, in other words, any capable of providing chloromethyl groups to replace the aromatic rings of the PC, can be used, for example, chloromethyl methyl ether/zinc chloride, chloromethyl methyl ether/$SnCl_4$, chloromethyl methyl ether/fuming $H2SO_4$, chloromethyl methyl ether/$TiCl_4$, paraformaldehyde/ZnCl/HCl, methoxyacetyl chloride/$AlCl_3$, methoxyacetyl chloride/$SnCl_4$, etc. The nucleophilic replacement reaction makes it possible to replace the chloride groups added in stage a) with one of the amino groups of the aliphatic diamine, the other amino group being left as a terminal amino group of the molecule. Practically any aliphatic diamine can be used; nevertheless, in one particular embodiment, the aforesaid aliphatic diamine is ethylenediamine. Other aliphatic diamines which can be used are propylenediamine or hexaethylenediamine, although, as has been previously mentioned, any compound with an aliphatic diamine structure could be used.

Once the PC surfaces are functionalized with amino groups or with molecules comprising a terminal amino group, these surfaces then undergo a chemical modification process by means of treating them with an aqueous solution of a mercaptoalkanoic acid of formula (I), the salts or derivatives thereof for the purpose of introducing thiol groups onto said surfaces (thiolyzation) and obtaining a PC surface with terminal thiol groups. In one particular embodiment, the compound of formula (I) is selected from between 3-mercaptopropionic acid (n=3) and 11-mercaptoundecanoic acid (n=11). This thiolyzation reaction is advantageously carried out in the presence of a coupling agent which serves as the compound activating the acid group to form the amide, for example, EDC/NHS, EDC/NHSS, DCC/NHS, etc.

Scheme 1 provides an outline of the different stages leading to obtaining PC surfaces functionalized with terminal thiol groups according to one particular embodiment of this invention.

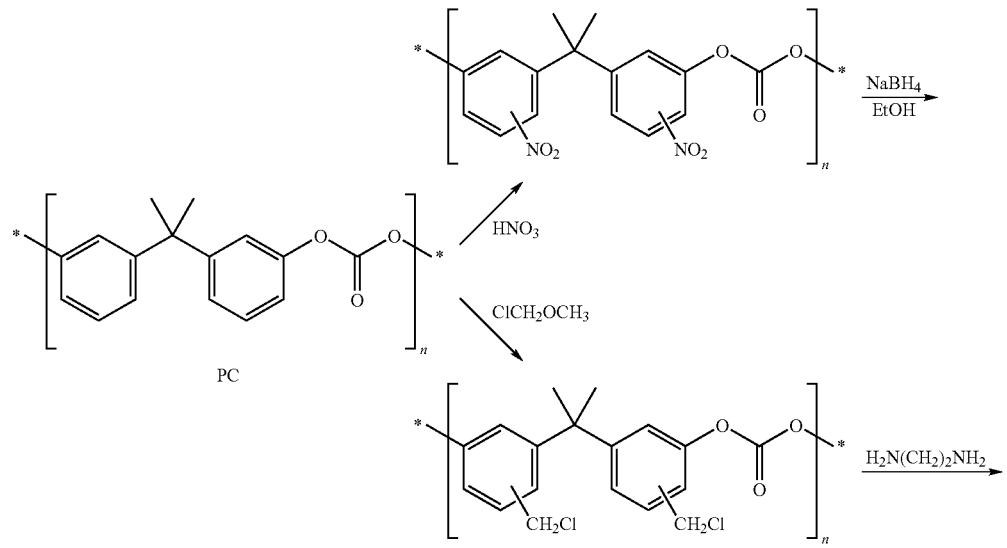

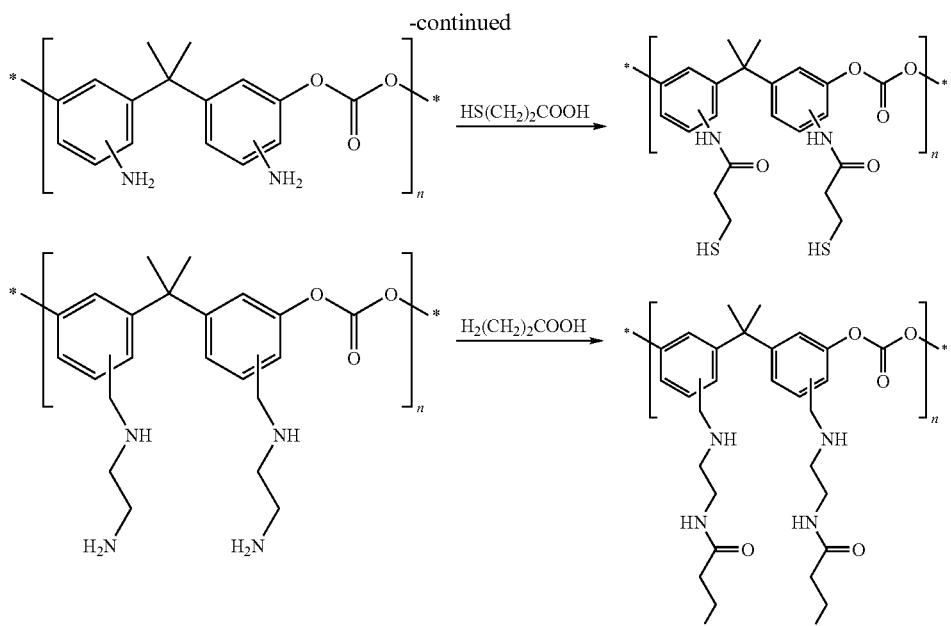

In another particular embodiment, the invention method comprises the use of a PMMA surface functionalized with molecules comprising terminal primary amino groups. The functionalizing of PMMA surfaces with molecules comprising terminal amino groups can be carried out by means of any procedure known to an expert in the art which makes it possible to introduce into the PMMA structure a molecule with a terminal amino group by way of the ester group. In one particular embodiment, this functionalizing is carried out by means of reductive amination of the methyl ester groups of the PMMA with an aliphatic diamine. Although practically any aliphatic diamine can be used, in one particular embodiment, said aliphatic diamine is ethylenediamine, propylenediamine or hexaethylenediamine, although virtually any compound with an aliphatic diamine structure could be used.

Once the PMMA surfaces are functionalized with molecules comprising terminal primary amine groups, the chemical modification of said surfaces is carried out by treating these surface with an aqueous solution of a mercaptoalkanoic acid of formula (I), the salts or derivatives thereof, thus obtaining a PMMA surface functionalized with terminal thiol groups. In one particular embodiment, the compound of formula (I) is selected from between 3-mercaptopropionic acid (n=3) and 11-mercaptoundecanoic acid (n=11). This reaction is advantageously carried out in the presence of coupling agents which serve as acid-activating compounds, such as EDC/NHS, EDC/NHSS, DCC/NHS, etc.

Scheme 2 provides an outline of the stages leading to obtaining PMMA surfaces functionalized with terminal thiol groups according to one particular embodiment of this invention.

Scheme 2

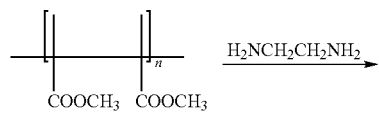

The presence of the terminal thiol groups on the functionalized PC and PMMA surfaces can be verified by using different tests for qualitative detection in solid phase synthesis (Ellman's test; Qualitative colorimetric tests for SPS (Solid Phase Synthesis) "Methods in enzymology", Vol. 369, 2003, 21-35), as well as by way of ATR-FTIR (Alternated Total Reflectance, Fourier Transform Infrared), EPS (Electron Dispersion Spectroscopy), fluorescence and angle of contact measurement techniques. The results indicate that the derivatization sought is achieved with good performance in all cases, it being generally assumed that the reaction is effective enough to generate a density of thiol groups suitable for assuring the covalent anchoring of the biomolecules. In addition thereto, the surface treated also displays an acceptable degree of homogeneity.

The presence of the thiol groups makes the subsequent covalent immobilization, such as nucleic acids (e.g. probes) or proteins, of biomolecules possible by way of disulfide bonds.

The PC or PMMA surfaces coated with a metal layer are PC or PMMA surfaces on which a layer of a metallic material has been deposited. This metallic material can be deposited by means of any technique known to an expert in the art, for example, by means of electrodeposition. In one particular embodiment, the aforesaid metal layer covering the PC or PMMA surface is a gold layer. The metal layer may vary in thickness over a wide range, typically within the 100-125 nm range.

Chemically modifying the PC and PMMA surfaces coated with the aforesaid metal layer can be carried out by submerging said surfaces, immediately following the deposition of the metal layer, into an alcohol solution of said mercaptoalkanoic acid of formula (I), the salts or derivatives thereof, for the purpose of forming an organic single layer. In one particular embodiment, said alcohol solution is an ethanol solution, and the mercaptoalkanoic acid of formula (I) employed is 11-mercaptoundecanoic acid. Next, the acid groups formed on the metalized surface are then activated by means of adding SDC/NHS, EDC/NHSS or DCC/NHS, thus making the subsequent anchoring of the biomolecules by way of their amine or hydroxyl groups possible, an amide bond or an ester respectively being formed.

Scheme 3 provides an outline of the stages leading to obtaining metalized PC or PMMA surfaces functionalized with acid groups according to a method of this invention:

Scheme 3

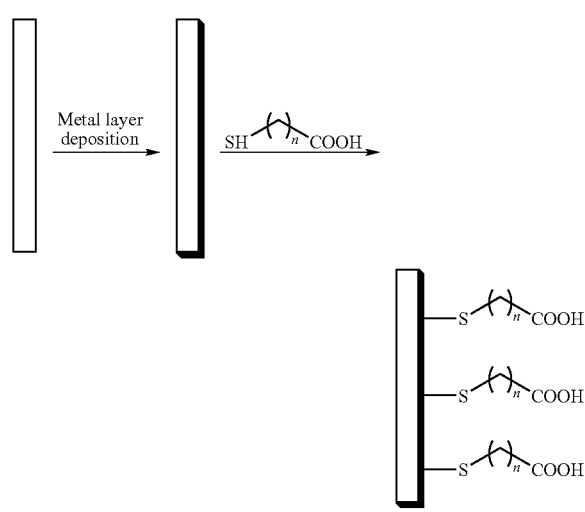

In another aspect, this invention provides a method for chemically modifying PMMA surfaces which makes the derivatization of said surfaces with thiol groups possible. Said method initially comprises treating the PMMA surface with a suitable reducing agent, such as a metal hydride, for example, lithium aluminum hydride, lithium borohydride, etc. or a Grignard reagent such as methyl magnesium bromide, in a suitable solvent, for example, cyclohexane, such that the ester groups are reduced to alcohol groups. The use of cyclohexane as a solvent seems to be of major importance, given that it makes it possible for the reduction reaction to take place without causing any swelling, deformation or loss of transparency of the polymer as occurs with other solvents commonly employed in the state of the art, such as ethyl ether.

Once the ester groups have been reduced, the surface is then treated with an alcohol solution of an organosilane comprising a terminal thiol group of formula (II).

$$HS-(CH_2)_m-Si-(OR)_3 \qquad (II)$$

where

"R" is methyl or ethyl, and

"m" is a whole number from 1 to 11.

In one particular embodiment, the compound of formula (II) used is (3-mercaptopropyl)-trimethoxysilane [$HS(CH_2)_3Si(OCH_3)_3$] in isopropanol.

Scheme 4 outlines the stages leading to obtaining PMMA surfaces functionalized with thiol groups according to one particular embodiment of this invention:

Scheme 4

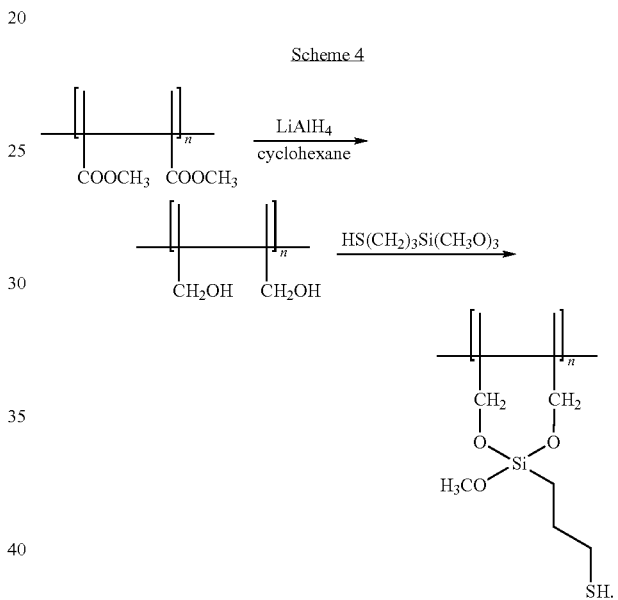

The presence of thiol groups, as previously mentioned hereinabove, affords the possibility of the then covalently immobilizing biomolecules, for example, nucleic acids or proteins, by way of disulphide bonds.

In another aspect, this invention relates to a solid support, referred to hereinafter as the functionalized solid support of the invention, comprising an optionally metalized PC surface or PMMA surface chemically modified according to the invention method. The functionalized solid support of the invention can be obtained from any solid support the surface of which is comprised, in full or in part, by PC or PMMA, optionally coated with a metal layer. The aforesaid functionalized solid support will advantageously also afford the possibility of the penetration and reflection of a beam of light, for example, a laser light beam, for the detection and reading of the data recorded on said support. Illustrative, non-limiting examples of the aforesaid solid supports include PC chips, PMMA chips, metalized PC chips, metalized PMMA chips, audio compact discs, video compact discs, audio-video compact discs, recordable or re-recordable CD, CD-ROM, CR or DVD discs, which make it possible to store the data which can then be read by means of a reading device by means of light beam penetration and reflection. In one particular embodiment, the aforesaid solid support is a re-recordable CD the surface of which is coated with a layer of gold. In general, a CD is approximately 1.2 mm in thickness and approximately 120 mm in diameter, although there are also smaller solid supports which can be adapted for specific applications. The thickness can be adapted in keeping with the technical requirements of the support to be functionalized, the biomolecule to be immobilized and the detection method to be employed. Thus, there are commercial discs measuring 6-3 cm in diameter and rectangular in format, like credit cards. As regards thickness, thicknesses of 1-0.6 mm can be used, the former being the most widely-known.

One or more biomolecules can be immobilized on the functionalized solid support of the invention. Therefore, in another aspect, the invention relates to a functionalized solid support of the invention which additionally comprises one or more biomolecules immobilized on said functionalized solid support of the invention. In one particular embodiment, the aforesaid functionalized solid support of the invention comprises one sole biomolecule immobilized thereon, whilst, in another particular embodiment, said functionalized solid support of the invention comprises a number of biomolecules immobilized thereon. Thus, the number of biomolecules to be immobilized may vary from one to tens of thousands depending on the assay, the immobilization density and the mode of immobilization.

In one particular embodiment, the aforesaid biomolecule is a nucleic acid probe, such as a DNA probe or an RNA probe (riboprobe). In another particular embodiment, the aforesaid biomolecule is a protein or an antibody or any substance which can be used under the principle of molecular recognition (molecular receptors, enzymes, carbohydrates, etc.).

In one particular embodiment, the aforesaid solid support comprises an optionally metalized PC or PMMA surface chemically modified according to the methods of the invention which comprises a biomolecule. In one particular advantageous embodiment, the aforesaid support also permits the penetration and reflection of a light beam, for example, a laser light beam, for the detection and reading of the data recorded on the aforesaid support disc. Illustrative, non-limiting examples of said solid supports include PC chips, PMMA chips, metalized PC chips, metalized PMMA chips, audio compact discs, video compact discs, audio-video compact discs, recordable or re-recordable CD, CD-ROM, CR or DVD discs, which make it possible to store the data which can then be read by means of a reading device by way of light beam penetration and reflection. In one particular embodiment, the aforesaid solid support is a re-recordable CD the surface of which is coated with a layer of gold. In general, a CD is approximately 1.2 mm in thickness and approximately 120 mm in diameter, although there are also smaller solid supports which can be adapted for specific applications. The thickness can be adapted in keeping with the technical requirements of the biomolecule to be immobilized and the detection method employed.

In one particular embodiment, the aforesaid biomolecule is a nucleic acid probe, and a single probe or a number of probes can be covalently immobilized by conventional methods on the functionalized solid support of the invention. These nucleic acid probes are fragments of genetic material selected from among sequences of oligonucleotides, genomic DNA (gDNA) or complementary DNA (cDNA) which may be natural or synthetic, although they are not limited exclusively thereto. The problem substances, complementary to the probes, will generally be marked for their direct or indirect detection. In one particular embodiment, these probes are marked with an enzyme (e.g. alkaline phosphatase, peroxidase, etc.), with a radioactive isotope (e.g. $^{33}P$, $^{125}I$, etc.), with a fluorochrome (e.g. fluoroscein, etc.), or rather with metallic particles for the direct detection thereof respectively by means of colorimetry, auto-radiography, fluorimetry or metallography or, alternatively, with a member of a binding pair (e.g. biotin, digoxygenin, etc), and the other member of the binding pair conjugated with a fluorochrome or with an enzyme for the indirect detection thereof by means of fluorimetry, (chemi)luminescence, etc. being added to the sample.

In another particular embodiment, the aforesaid biomolecule is a protein (e.g. a structural protein, antibody, an enzyme, a molecular receptor, etc.) and a single protein or a number of proteins can be covalently immobilized by conventional methods on the functionalized solid support. These proteins will generally be marked for their direct or indirect detection. In one particular embodiment of the invention, these proteins will be linked to a fluorochrome or to a member of a binding pair, the other member of the binding pair conjugated with an enzyme or with a fluorochrome, etc. being added to the sample for the detection thereof by colorimetric or fluorimetric methods analogous to those described in the immediately preceding paragraph hereinabove.

In another particular embodiment, the aforesaid biomolecule is a cell membrane, such as a plasma membrane, a nuclear membrane or a membrane of any cell organelle, and a single cell membrane or a number of cell membranes can be covalently immobilized by conventional methods on the functionalized solid support of the invention. The aforesaid membranes can be marked for their direct or indirect detection by conventional methods.

The aforesaid functionalized solid support of the invention may therefore be used as a support for an array or for a microarray of biomolecules, thus comprising a two-dimensional matrix on which the desired biomolecules are immobilized in an established order and arrangement. The aforesaid array or microarray of molecules affords the possibility of applications including the simultaneous, comparative analysis of the expression of numerous genes in one single experiment, etc.

The biomolecules can be immobilized on the functionalized solid support of the invention by conventional methods known to experts in the art.

In another aspect, this invention relates to the use of a functionalized solid support for the immobilization of biomolecules.

In another aspect, this invention relates to a method for immobilizing biomolecules on a solid support which comprises bringing said functionalized solid support of the invention into contact with a biomolecule.

The immobilization of the aforesaid biomolecules can be carried out by means of conventional conditions well-known in the state of the art [Sambrook et al., 9.31-9.58 in *Molecular Cloning*: A Laboratory Manual, Cold Spring Harbor, Laboratory Press, New Cork (1989)]. These biomolecules contain, either naturally or by means of a modification method, a functional chemical group (amino, sulfhydryl, aldehyde, etc.) making their bonding and immobilizing on the optionally metalized PC or PMMA surface chemically modified by means of the invention method possible. The immobilizing of the biomolecules on the aforesaid modified polymer surfaces takes place by means of a covalent bond with the formation of disulphide bridges in the case of using PC or PMMA surfaces modified with thiol groups. In the case of using metalized PC or PMMA surfaces modified with acid groups, the biomolecules are immobilized by means of a covalent bond with the formation of amide or ester groups, depending upon whether the biomolecule is fixed by way of an amino group or by way of an alcohol group.

The following examples illustrate this invention, however must not be considered limiting of the scope thereof.

EXAMPLE 1

Chemical Modification of a Polycarbonate (PC) Surface

The method comprises two stages, a first amination stage, which can be carried out according to two different methods (Methods A and B), and a second thiolyzation stage.

Stage 1: Amination
Method A: Nitration+Reduction

Polycarbonate chips (in other words, chips the surfaces of which were polycarbonate) were fully immersed into a 30% nitric acid aqueous solution for 1 hour at 80° C. During the process, a color change from a colorless to a yellow substance was observed. The chips were washed with abundant distilled water. For the purpose of reducing the nitro groups, the chips were fully immersed into a 10% $NaBH_4$ ethanol solution and were left at ambient temperature for 16 hours. Lastly, they were washed first with ethanol and then with distilled water.

Method B: Chloromethylation 2 g $ZnCl_2$ and 2 ml chloromethyl methyl ether were added to a round-bottomed flask containing the polycarbonate chips fully immersed in cyclohexane (80 ml). This mixture was left to react for 2 hours at 60° C., chloromethylated polycarbonate surfaces having been obtained, Which were then washed with distilled water. The chloromethylated polycarbonate surfaces were allowed to react with 2M ethylenediamine (70 ml) for 2 hours at ambient temperature. They were then washed with distilled water and dried. Lastly, the ninhydrine test was used to check to ensure that the reaction had successfully taken place.

Stage 2: Thiolyzation

The polycarbonate chips functionalized with amino groups (aminated polycarbonate chips) previously obtained in Stage 1 (Methods A and B) were fully immersed into a solution of 5 mM EDC, 0.33 mM NHSS and 5 mM 11-mercaptoundecanoic acid, a 0.1 M MES buffer, pH 6.5 (100 ml) and we allowed to react at ambient temperature for 3 hours. The chips were washed first with water and then with ethanol, after which they were dried. The existence of thiol groups in the treated chips was detected by means of the Ellman's test.

EXAMPLE 2

Chemical Modification of a Polymethacrylate (PMMA) Surface

This method comprises two stages, a first amination stage, which can be carried out according to two different methods (Methods A and B), and a second thiolyzation stage which was carried out following two different methods (Methods I and 11).

Stage 1: Amination
Method A: Treatment with Organosilane

The PMMA chips (in other words, chips the surfaces of which were polymethacrylate) were first washed thoroughly with ethanol and were then dried. Next, these chips were fully immersed into a mixture of $LiAlH_4$ (0.9 g) in cyclohexane anhydride (30 ml) and were allowed to react all night at ambient temperature in a dry atmosphere. The excess $LiAlH_4$ was carefully hydrolyzed with methanol, and the chips were washed with HCl (10%), water and ethanol and were then air current dried. For the incorporation of the organosilane, the chips were fully immersed into a solution of (3-aminopropyl)-trietoxy-silane in 2-propanol and were left in ultrasound (Ultrasons Selecta) for 1 hour. Next, they were washed thoroughly with ethanol/water and then dried. To confirm the presence of amino groups on the PMMA surfaces, the ninhydrine test was used.

Method B: Amide Attack 3 ml 2M lithium butyl in cyclohexane were added to a flask under argon atmosphere. The solution was cooled to 0° C., and 1.2 ml ethylenediamine were carefully added. This mixture was left at 0° C. for 3 hours. Next, 20 ml of cyclohexane were added along with the PMMA chips, previously washed with ethanol and then thoroughly dried, allowing them to react for 20 minutes. Next, the mixture was poured onto water, and the chips were washed with water/ethanol and then dried. The presence of amino groups was confirmed by means of the ninhydrine test.

Stage 2: Thiolyzation
Method I: Treatment with Organosilane

The PMMA chips were washed thoroughly with ethanol and were then dried. Next, they were fully immersed into a mixture of $LiAlH_4$ (0.9 g) in cyclohexane anhydride (30 ml) and were allowed to react all night at ambient temperature in a dry atmosphere. The excess $LiAlH_4$ was carefully hydrolyzed with methanol, and the chips were washed with HCl (10%), water and ethanol and were then air current dried. For the incorporation of the organosilane and for the purpose of obtaining PMMA surfaces modified by means of thiol groups, the chips were fully immersed into a solution of 10% (3-mercatopropyl)-trimethoxysilane in propanol and were left in ultrasound (Ultrasons Selecta) for 1 hour. Next, they were washed thoroughly with ethanol/water and then dried. To confirm the presence of thiol groups on the modified PMMA surfaces, the Ellman's test was used.

Method II: Coupling with 11-mercaptoundecanoic Acid

Following the same method as described for the thiolyzation of the aminated polycarbonate (Example 1, Stage 2), the PMMA chips modified with amino groups previously obtained (Example 2, Stage 1, Methods A or B) were fully immersed into an aqueous solution containing 5 mM EDC, 0.33 mM NHSS and 5 mM 11-mercaptoundecanoic acid, in 0.1 M MES buffer, pH 6.5. They were left in ultrasound for 3 hours and were then washed and dried. The presence of free thiol groups was detected by means of the Ellman's test.

EXAMPLE 3

Generation of Aldehyde Groups on Polycarbonate (PC) and Polymethacrylate (PMMA) Surfaces by Means of Cross-Linking with Glutaraldehyde Starting from the aminated PC and PMMA chips (in other words, functionalized with amino groups) obtained in Example 1 (Stage 1) and in Example 2 (Stage 1), aldehyde groups were generated as described in following. The chips were fully immersed into an aqueous glutaraldehyde solution (5% PBS 0.1 M, pH 6.5) and 5% trimethylaminoborane (TMAB) and were left in ultrasound for 2 hours at ambient temperature. Lastly, they were washed thoroughly with ethanol and then dried. To confirm the existence of aldehyde groups, both the Tollen's test as well as the anisaldehyde test were used. The surfaces thus prepared were later used in the preparation of DNA arrays.

EXAMPLE 4

Modification of Surfaces on Gold CDs

The modification of surfaces on gold CDs was carried out by means of a method comprising the activation of the surfaces and the reduction of the acid group.

Stage 1: Activation of the Surfaces with Mercaptoundecanoic Acid

For carrying out this stage, the gold CDs were activated by immersion in concentrated $HNO_3$, were then washed in water and air current dried. Next, the gold CDs were fully immersed into a solution of 1 mM 11-mercaptoundecanoic acid in ethanol and were left 24 hours at ambient temperature.

The same method was followed with PC plates, on which a layer of gold differing in thickness depending on the exposure time to the gold, which ranged from 30-180 s, was electrodeposited. In all cases, the forming of the single gold layer was tested by cyclic voltamperometry.

Stage 2: Reduction of the Acid Group

The plates obtained in Stage 1 hereinabove were fully immersed into a solution of 5 mM EDC and 0.33 mM NHSS in 0.1 M MES buffer, pH 6.5 and were left in ultrasound at ambient temperature for 2 hours. They were then washed thoroughly with water and then dried.

EXAMPLE 5

Oligonucleotide Immobilization

Oligonucleotides with terminal amino groups and oligonucleotides with terminal thiol groups were immobilized by means of the methods described hereinbelow. The immobilization of the oligonucleotides was detected, in both cases, by means of a fluorescence scanner.

Oligonucleotide Immobilization

A) Oligonucleotides with Terminal Amino Groups

Solutions of oligonucleotides marked with the Cy5 group (1 and 10 μM) were prepared by employing different types of solvents: 1×SSC pH 7, 10×SSC pH 7, 1×TC pH 9.6, 10×TC pH 9.6, 1×PBS pH 11 and 1×PBS pH 11. Next, 3×3 arrays were contact-printed with each one of the aforesaid solutions previously prepared. The arrays were allowed to incubate in a wet chamber at 42° C. for 2 hours or for 4 hours at ambient temperature. Next, they were fully immersed into a solution of 5% $NaBH_4$ in PBS/EtOH 75/25, pH 6.5 and were left in ultrasound for 10 minutes. Lastly, the arrays were washed thoroughly with water and then dried.

The surfaces of the arrays tested were as follows:
PC surface aminated (Example 1, Stage 1, Method A) and treated with glutaraldehyde (Example 3); and
PMMA surface aminated by organosilane treatment (Example 2, Stage 1, Method A) and treated with glutaraldehyde (Example 3).

Non-derivatized plates and non-functionalized oligonucleotides were used as controls.

B) Oligonucleotides with Terminal Thiol Group

The terminal thiol group of the oligonucleotides was linked to the thiolated surfaces by means of a layer of mercaptosilane and by means of the thiol-disulphide exchange reaction. The oligonucleotides marked with the Cy5 group were diluted to 1 μM in carbonate buffer 0.1 M pH 9, PBS 1×pH 8, PBS-T 1×pH 8 and 1×SSC pH 4.5. Next, 3×3 arrays were contact-printed with each one of the aforesaid solutions previously prepared. The arrays were allowed to incubate for 2 hours at ambient temperature and were then washed with PBS-T 1×pH 7.5 and then dried.

The surfaces of the arrays tested were as follows:
PC surface modified with thiol groups (Example 1, Stage 2); and
PMMA surface modified with thiol groups by treatment with organosilane (Example 2, Stage 2, Method I) and treated with glutaraldehyde (Example 3).

Non-derivatized plates and non-functionalized oligonucleotides were used as controls.

Detection of Oligonucleotide Immobilization

The immobilization of the oligonucleotides was detected, in both cases, by means of a Genepix 4000B fluorescence scanner by Axon Instruments (Union City, Calif., USA) at $\lambda_{exc}$ 635 nm and $\lambda_{em}$ 670 nm.

In all cases, the covalent immobilizing of the oligonucleotides to the arrays (plates) treated according to the invention method were found to provide a higher intensity of fluorescence and a better signal-to-noise ratio than the oligonucleotides anchored to plates by means of unspecific interactions (control samples).

These immobilization studies revealed that the treated polymer surfaces employed provided a better result compared to other surfaces (e.g. glass surfaces comprising the plates). Employing optionally metalized PC and PMMA surfaces reveals the possibility of applying the biomolecule derivatization and immobilization methodologies on compact discs, given that these polymers are the main ones of which commercial CDs are comprised.

On comparing the surface modification methods of this invention to other coating methods such as avidin or polylysine, the methods of this invention were found to have the advantage of providing a much stronger bond which better withstands the washing processes and is longer-lasting over the course of time by substituting the electrostatic interactions as well as the hydrophilic/hydrophobic interactions for covalent bonds which are irreversible in most cases.

The invention claimed is:

1. A method for chemically modifying a polymer surface, selected from among (i) a polycarbonate (PC) surface functionalized with primary amino groups or with molecules comprising terminal primary amino groups and (ii) a polymethacrylate (PMMA) surface functionalized with molecules having terminal primary amino groups, said method comprising reacting said polymer surface with a carboxylic group of a mercaptoalkanoic acid of formula (I)

$$HS-(CH_2)_n-COOH \qquad (I)$$

where "n" is a whole number from 3 to 11;
its salts or derivatives thereof.

2. Method according to claim 1, wherein the treatment with the mercaptoalkanoic acid is carried out in the presence of a coupling agent.

3. Method according to claim 2, wherein said coupling agent is selected from among
1-ethyl-3-(3-dimethylaminopropyl) carbodiimide (EDC)/N-hydroxy succinimide (NHS);
EDC/sulfa-N-hydroxy-succinimide (NHSS); and
Dicyclo-hexylcarbodiimide (DCC)/NHS.

4. Method according to claims 1, wherein said mercaptoalkanoic acid is either 3-mercaptopropionic acid or 11-mercaptoundecanoic acid.

5. Method according to claim 1, wherein the functionalizing of the PC surfaces with primary amino groups comprises the stages of:
(i) nitration of the aromatic rings comprising the structure of the PC, and
(ii) reduction of the nitro groups introduced in stage a), into amino groups.

6. Method according to claim 5, wherein the nitration of the aromatic rings is carried out with nitric acid.

7. Method according to claim 5, wherein the reduction of the nitro groups is carried out with a reducing agent selected from among NaBH₄, TMAB, BH₃-THF, Red-Al, DIBAH and LiAlH₄.

8. Method according to claim 1, wherein the functionalization of the PC surfaces with molecules containing terminal primary amino groups comprises the stages of:
   a) chloromethylation of the aromatic rings comprising the PC structure; and
   b) nucleophilic replacement of the chloride groups present following stage a) by reaction with an aliphatic diamine.

9. Method according to claim 8, wherein the chloromethylation of said aromatic rings is carried out with a chloromethylating agent.

10. Method according to claim 9, wherein said chloromethylating agent is selected from among chloromethyl methyl ether/zinc chloride, chloromethyl methyl ether/SnCl₄, chloromethyl methyl ether/fuming H₂SO₄, chloromethyl methyl ether/TiCl₄, paraformaldehyde/ZnCl/HCl, methoxyacetyl chloride/AlCl₃ and methoxyacetyl chloride/SnCl₄.

11. Method according to claim 8, wherein the aforesaid aliphatic diamine is selected from among ethylenediamine, propylenediamine and hexaethylenediamine.

12. Method according to claim 1, wherein the functionalization of the PMMA surfaces with molecules containing terminal primary groups comprises the amination of the methyl ester groups of the PMMA with an aliphatic diamine.

13. Method according to claim 12, wherein the aforesaid aliphatic diamine is selected from among ethylenediamine, propylenediamine and hexaethylenediamine.

14. A solid support comprising a PC or PMMA surface chemically modified by a method comprising reacting said polymer surface with a carboxylic group of a mercaptoalkanoic acid of formula (I)

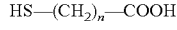   (I)

where "n" is a whole number from 3 to 11;
its salts or derivatives thereof.

15. Support according to claim 14, configured in the form of an optionally metalized PC or PMMA chip, an audio compact disc, a video compact disc, an audio-video compact disc, a recordable or re-recordable CD, CD-ROM, CR or DVD disc.

16. Support according to claim 14, comprises at least one biomolecule immobilized on said support.

17. Support according to claim 16, wherein said biomolecule is a nucleic acid, a protein, a substance which can be used in molecular recognition, a membrane or a cell fragment.

18. Support according to claim 17, wherein the aforesaid biomolecule is a nucleic acid, a protein, an antibody, a molecular receptor, an enzyme, a carbohydrate, a cell membrane or a cell fragment.

19. Support according to claim 14, comprising multiple types or species of biomolecules immobilized on said support.

20. Support according to claim 19, wherein the aforesaid multiple types or species of biomolecules are immobilized on said support in an established arrangement and order forming an array or a microarray.

21. A procedure for the immobilization of biomolecules comprising putting a solid support comprising a PC or PMMA surface chemically modified by a method comprising reacting said polymer surface with a carboxylic acid of a mercaptoalkanoic acid of formula (I)

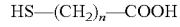   (I)

where "n" is a whole number from 3 to 11;
its salts or derivatives thereof; into contact with the biomolecules to be immobilized under conditions which permit the immobilization of the aforesaid biomolecules on said support.

* * * * *